(12) United States Patent
Shoutov

(10) Patent No.: US 8,524,293 B1
(45) Date of Patent: Sep. 3, 2013

(54) METHOD FOR PRODUCING A RED GRAPE TEA-LIKE COMPOSITION

(76) Inventor: Dmitriy Shoutov, Bronx, NY (US)

( * ) Notice: Subject to any disclaimer, the term of this patent is extended or adjusted under 35 U.S.C. 154(b) by 0 days.

(21) Appl. No.: 13/491,804

(22) Filed: Jun. 8, 2012

Related U.S. Application Data

(62) Division of application No. 12/383,714, filed on Mar. 26, 2009.

(51) Int. Cl.
| | | |
|---|---|---|
| *A61K 36/87* | (2006.01) | |
| *A61K 36/00* | (2006.01) | |
| *A23G 1/02* | (2006.01) | |
| *A23L 1/36* | (2006.01) | |
| *A23L 1/28* | (2006.01) | |
| *A23L 2/02* | (2006.01) | |

(52) U.S. Cl.
USPC ............. 424/766; 424/776; 424/777; 426/44; 426/51

(58) Field of Classification Search
None
See application file for complete search history.

(56) References Cited

U.S. PATENT DOCUMENTS

| | | | |
|---|---|---|---|
| 6,086,910 A | 7/2000 | Howard et al. | |
| 6,190,716 B1 * | 2/2001 | Galbreath, Jr. ................ | 426/443 |
| 6,470,894 B2 | 10/2002 | Hersh | |
| 6,479,081 B2 * | 11/2002 | Feries ........................... | 424/766 |
| 6,544,581 B1 * | 4/2003 | Shrikhande et al. .......... | 426/655 |
| 6,642,277 B1 | 11/2003 | Howard et al. | |
| 7,026,518 B2 | 4/2006 | Gokaraju et al. | |
| 7,087,259 B2 | 8/2006 | Wild et al. | |
| 7,273,607 B2 | 9/2007 | Schakel et al. | |
| 7,306,815 B2 | 12/2007 | Gourdin et al. | |

OTHER PUBLICATIONS

Hogan et al. (2010) Nutrition and Metabolism 7: pp. 71-80.*
Lu et al. (1999) Food Chemistry 1-8.*

* cited by examiner

*Primary Examiner* — Chris R Tate
*Assistant Examiner* — Russell Fiebig
(74) *Attorney, Agent, or Firm* — Andrew S. Langsam; Pryor Cashman LLP

(57) ABSTRACT

A method for producing a dry composition from red grapes by natural fermentation that is, once brewed, steeped within hot water, tasteful to ingest as herb tea, and that complementary contains antioxidants, Catechin, Resveratrol, Tannin, Quercetin bearing anti-inflammatory and blood glucose lowering capacities; as well as a human skin rejuvenating natural product derived there from. The method is used to prepare dry composition containing phenolic antioxidants such as catechin, resveratrol, and quercetin, and comprises small parcels made from the grape berry, stalks, skins and seeds of the red grape *Vitis labrusca*. The method uses the sequential steps of crushing, two successive natural fermentation periods, and drying by utilizing simplified operations.

11 Claims, No Drawings

METHOD FOR PRODUCING A RED GRAPE TEA-LIKE COMPOSITION

RELATED APPLICATIONS

The present application is a divisional of application Ser. No. 12/383,714, filed on Mar. 26, 2009, for Red Grape Dry Composition and Health Tea. The Examiner restricted the claims submitted in an amendment filed Dec. 19, 2011, directed to a method for making the product, and only examined the claim drawn to a composition.

BACKGROUND

1. Field of Invention

Red grape dry composition and health drink containing powerful antioxidants including resveratrol, for human consumption, and for skin topical application, the production thereof and use of the same.

2. Prior Art

This invention relates to a human food product that, due to its nutrient characteristics, contains many health benefits. It is suitable for human consumption in the form of a tea-like beverage as part of a normal daily diet, or in other forms as a food supplement. The invention is prepared by means of a unique, simplified method using stalks, skins, and seeds of red grape berries, which, combined together, naturally bear powerful anti-inflammatory properties when the ingredients are subjected to natural methods of fermentation and other natural processing.

Grape seeds and skins have been long under scrutiny by the scientific community for their strong antioxidant characteristics. Recent advances in medicine, biology, and other sciences have brought new light in a quest for longer, healthier human life span. One of the most important discoveries in the last ten years was a set of genes, called sirtuin, which is believed to play a critical role in regulating the lifespan. Chemicals that affect sirtuin activity have been found in plants, and one specifically, resveratrol, is viewed as notably powerful in the process of activating health-promoting genes.

Resveratrol is a phytoalexin produced naturally by several plants, including grapes (primarily in the seed and skins), apparently due to its anti-fungal reaction. Plants, e.g. blueberries, bilberries, peanuts and others, generate resveratrol, and it is, also present (in a wide range, 0.4-40 mg/L) in grape wines, especially reds. Grape pomace/marc (byproducts of winemaking), grapes juices, and wines are all used as a source for resveratrol extraction.

Resveratrol anti-inflammatory properties are utilized by pharmaceutical industries in the U.S. and overseas in making drugs and food supplements. Gokaraju et al. (U.S. Pat. No. 7,026,518, 2006) stated that antioxidant and superoxide scavenging properties of resveratrol have been scientifically established. Efforts are now being made to synthesize structural analogs of resveratrol for evaluation of their relative antioxidant potentials.

Cambridge based bio-pharmaceutical company, Sirtris, Inc. (NASDAQ: SIRT) is searching to develop a proprietary molecule drug to treat diseases associated with aging, including metabolic diseases such as Type 2 Diabetes. In January 2008, the company released results from recent clinical trials that found patients with diabetes who took the drug (SRT-501) showed improvement. The treatment is a concentrated form of resveratrol, a substance extracted from red wine. Sirtris hopes to bring its drug to market in 2012. (The Boston Globe, Jan. 10, 2008).

Furthermore, grape seeds and skins have a high concentration of other phenolic components that are also recognized for positive effects on human health: tannin (studies by Feries et al. (U.S. Pat. No. 6,479,081, 2002)), catechin, resveratrol, and quercetin (hereinafter "CRQ"), as well as vitamins and minerals. A number of U.S. patents were issued to inventions which discovered either new health-beneficial compositions, including grape seeds/skin processed derivatives, and/or offered innovative combinations and/or methods of their intaking Schakel et al. (U.S. Pat. No. 7,273,607, 2007) studied grape seed extract and recommended its usage in combination with other herbs and essential oils. Schakel's formula, including grape seed extracts, claimed to slow, stop, or reverse the growth of cancerous cells. Hersh, et al. (U.S. Pat. No. 6,470,894, 2002) suggested including grape seed extract into a composition to neutralize tobacco free radicals. Hersh and others revealed grape seeds' ability to reduce free radical damage to the oro-pharyngeal cavity, respiratory tract, and lungs resulting from tobacco smoke. Moreover, Wild, et al., (U.S. Pat. No. 7,087,259, 2006) demonstrated that the presence of oligomeric procyanidins in grape seed extracts makes them very efficient free-radical scavengers due to their hypotensive and antiarteriosclerotic properties.

Howard et al. (U.S. Pat. No. 6,086,910, 2000 & U.S. Pat. No. 6,642,277, 2003) conducted comprehensive studies with plant-derived polyphenols for human health benefits. The inventors showed, including through experiments on volunteers, positive therapeutic effect of their proprietary 25% polyphenol concentrate in critical human health areas, e.g. preventing or treating coronary heart disease; and inhibition of oxidation of plasma LDL and/or platelet aggregation. Howard et al. used grape wine, pomace (substance comprising grape marc and juice prior to pressure-separating) among their sources for preparing polyphenol powder. The inventors, furthermore, used the following methods to extract resveratrol: a) vacuum distillation at 75-80 degrees C., and b) nitrogen drying.

Many, if not all, of the essential characteristics of grape seeds and skins described in the aforementioned inventions, such as the ability to neutralize inflammatory processes, to slow the growth of cancerous cells, and others, should safely exist in the new composition of the substance of the present invention, i.e. dry grape berry stalks, skins and seeds and health drink made therefrom. The present invention greatly differs from findings and products currently available in scientific and practical fields.

Most patents reviewed target novel compositions of prescribed drugs for hospital patients, while the prime objective of the present invention is a natural plant composition designed for prophylactic and prevention treatment. In the food supplements field, reviewed patents (e.g. Wild et al. U.S. Pat. No. 7,087,259) cover mostly grape seed/skin extracts without the inclusion of the grape berry stalks, which is an important distinction of this invention. None of the observed patents or products available on the market matches the uniqueness of the present invention either in terms of the combination of grape plant parts, or in terms of originality of preparation method involving natural fermentation. For instance, Howard et al., by using, as a source, commercially obtained wine or pomace (that were other makers' products), subjected themselves to a greater chance of uncertainty. Advantageously, findings of the present invention benefit from having raw grape plants, Concord Grapes from the Finger Lakes region of the U.S., as its initial source. Thus, while viewing the wine as a source for polyphenols and resveratrol, an intriguing connection is found between the wine making method (whether or not it was fermented and mixed with skins, seeds and stems/stalks) and the amount of resveratrol found in the final substance. For instance, Spanish wines tend to be resveratrol-richer due to the fact that local wine-makers, historically, preferred to ferment crushed grapes mixed with skins, seeds, and stalks, for a relatively longer time.

Also, it looks like a similar method was used by Stone Age people, 8,000 years ago, in Shulayeri village in Georgia (Caucasian Mountain) where the world's oldest wine was recently found. Hence, with regard to fermenting, this invention employed a method similar to ancient traditions, i.e. a) three components of a grape plant: grape berry stalks, skins and seeds were used in the mixture for fermentation; and b) an extended fermenting period, up to three weeks, was employed. This technique is based on an existing hypothesis that biological and chemical reactions during pomace/marc fermentation provide a favorable environment for preserving, or even enriching phenolic antioxidants, including resveratrol, in the substance. Furthermore, words of caution should be expressed with regard to techniques used by researchers to extract antioxidants. Specifically, Gourdin, et al. (U.S. Pat. No. 7,306,815, 2007) studied the enrichment methods of phenolic compounds and concluded that a hot extraction temperature can cause degradation of the proanthocyanidins. In addition, it was found that the ultrafiltration removes some of the low molecular weight polyphenolic material from the final product.

A Napa Valley (CA) based company sells assorted "Antioxidant Grape Seed Spa Teas" that are worth review as remotely comparable to the composition of this invention. The sample we tasted had the following ingredients: wine grape seeds, rose petals, chamomile, orange peel, stevia and natural fruit oils. Whether there were antioxidants, and if so their levels, was not indicated on the label. The findings of physical examination showed that the grape seed content in the composition of the 2 g tea bag was about 10-15%. This means that the composition would contain a proportional amount of phenolic antioxidants, i.e. 10-15% per 2 g tea bag, given that Napa Valley used CRQ potent grapes. Neither grape skins nor stalks have been found in "Grape Seed Spa Tea." Thus, many manufacturers choose to present and advertise their product using just general terminology. In some cases, they would refer to resveratrol or other antioxidant contents in an original fruit or plant source, not in a final product. Advantageously, the present inventive composition is to consist of 80-100% of red grape stalks, skins, and seeds which contain a potent group of phenolic antioxidants (HPLC) that are proven to be present in the final product as well as in its original natural source.

Besides resveratrol, catechin, quercetin, and tannin are present in the composition of the present invention. These substances have also been found to have positive effects on the human immune system in different trials. Weyant et al. studied the implications of catechin on a cancerous mouse to conclude that catechin inhibited intestinal tumor formation and "suppressed focal adhesion kinase activation." (Cancer Research (ISSN 0008-5472), 61, 118-125, Jan. 1, 2001, by the American Association for Cancer Research, Inc. (AACR)). J. Mark Davis (Professor and Director of Exercise Biochemical Laboratory, University of South Carolina) named quercetin a powerful antioxidant shown to reduce the risk of flu in laboratory animals. Recent studies have also shown the capacity of tannins to suppress production of the peptides responsible for hardening arteries, as well as other potential antiviral, antibacterial and antiparasitic effects. In the past few years, tannins have also been studied for their potential effects against cancer through different mechanisms.

Furthermore, phenol products, especially grape seed oil, are known to be able to prevent ultraviolet light-induced damage to human hair and skin and otherwise rejuvenate facial and body skin. The cosmetics industry uses these properties in manufacturing sunscreens, body scrub cleansing, hair dyes and others. According to a London-based market research firm "Mintel International Group, Ltd," grapes are widely used in the cosmetics industry because of their "anti-aging" properties. ("Grapes boast high potential in anti-aging market" by Guy Monatgue-Jones, Aug. 2, 2008, available at www.cosmeticsdesign.com). One of many facial moisturizes available on the market, "Merlot. Grape Seed Moisturizer" by Merlot, a US company, was examined by the inventor of the present invention. As per the trade label, the main ingredient was 'grape seed polyphenols." No grape skins or stalk derivatives were said to be present in the product. Numerous other cosmetic products and related publications were reviewed in order to determine whether any of them offer, recommend or refer to the usage of the ingredient complex similar to those suggested by the present invention. Nothing was found resembling the uniqueness of the present invention composition and the method of its preparation.

SUMMARY OF THE INVENTION

The present invention discloses a unique antioxidant drink and method of its preparation. The ultimate goal of this invention is to provide health-minded people with new natural products, namely, red grape dry composition, health tea or drink, and derivative human skin rejuvenation materials, that <can be inexpensively made by small and medium size vineries and even by individual entrepreneurs at properly equipped home kitchens.> The philosophical basis of the invention lies in following natural methods of processing the grapes: crushing, fermenting, drying, boiling, and steeping, and completely excluding the usage of any catalysts, chemicals or artificial additives.

The socioeconomic importance of the current invention emerges from the fact that the source, the Concord Grape (*Vitis labrusca*), is a native plant to the Eastern United States and is naturally growing in abundance in the Continental climate of the Northern part of New York. This variety of grape is not popular among winemakers due to the fruity aroma of the berry and limited sweetness that contributes to an overall "flat" body of wines. At the same time, due apparently to the fact that this plant was exposed to harsh ecological challenges, it embodies botanical survival characteristics which consequently transfer to humans strong anti-inflammatory capacities. Potent polyphenolic properties of Concord grapes have not yet been fully studied. Obviously, this grape variety was underappreciated not only by winemakers but also by resveratrol-researchers who, often, name Malbec, Petite Sirah, St. Laurent, Pinot Noir and other exotic variety among resveratrol-richest grapes (Ref. F. Breton, "Polyphenols in Red Wine"). The same author points out that "vine grapes grown in cooler climates have higher resveratrol levels than those from warmer climates."

With the overall economy struggling in recent years, the grape growing and wine industries of the New York region have been experiencing great challenges. Hence our new product made by a noncapital intensive method from the source of the wine industry byproduct can well contribute into new economic development model pursued by the regional governments.

One of the preferred embodiments, grape health tea or beverage, is pleasantly drinkable in a form of a hot or cold herbal tea with a woody aroma, or mixed with a physiologically acceptable food items. Furthermore, the invention importantly discovers a possibility of achieving higher HPLC (polyphenolic antioxidants) concentration by repeating established processing procedures with a greater amount of source material per fixed or smaller volume of water.

Moreover importantly, the preferred embodiment demonstrated anti-inflammatory potency in assisting in the speedy recovery of volunteers suffering from Influenza. In another case, treating individuals with the grape beverage led to considerable lowering of their blood glucose levels. Healthy adults would pleasantly ingest such grape beverage as a food item similar to herbal tea, while people suffering from different medical conditions would be able to take such drink as a supplement to prescribed medications to improve their body's overall resistance to disease.

DETAILED DESCRIPTION OF THE PREFERRED EMBODIMENTS

The following describes the preferred embodiments of the present invention, which should not be viewed as a limitation to the whole invention. It should be understood that if further details, specifics, or nuances are to be developed within the frame of the present invention concept, those too will be considered integral parts to the present invention.

(a) Embodiment: Red Grape Dry Composition and the Method of its Preparation.

To prepare the red grape dry composition, Concord grapes were used, which were conveniently purchased in a Finger Lake region vineyard (New York State, USA).

The grape berries were crushed, mixed with berry stems and stalks, and placed in a stainless steel vat for fermenting. Some seeds were intentionally crushed, but not more than 7-10%, whereas the rest were left to ferment in their entirety. The content consisting of a liquid phase (juice or mush) and solid phase (skins or cuticles of the berries, berry stalks/stems, seeds or pomace/marc) was allowed for primary natural fermentation for a period of 8 (eight) days. During this time, ambient yeasts naturally present on the grapes and stems catalyzed the process.

Contrary to prior art inventors, no acidity adjusting chemicals (like sodium hydroxide or potassium metabisulfite from commercial winemaking) were used. Within the first 24 hours of fermentation, lighter parcels formed a "cap" which was punched down twice a day, and at the same time the whole content was thoroughly mixed. This segment of fermentation was conducted at room temperature, 72° F. At the end of eighth day, when active bubbling slowed down, the juice was separated from the pomace/marc by pressing. The solids, consisting of skins, berry stalks/stems, and seeds, and with a limited amount of juice, were left for another 7 (seven) day secondary fermentation. Thorough stirring was performed twice a day. Secondary fermentation was conducted at a lower temperature than primary fermentation, namely 60° F. On the 16$^{th}$ (sixteenth) day since the commencement of the initial fermentation process, the pomace/marc, i.e. skins, seeds, berry stalks and some stems, still high in moisture, was further pressed to eliminate residual watery content, and was exposed to sun-drying for 6 hours followed up by oven drying. The oven drying was performed at 180° F. for about 10 hours to achieve a water activity at 0.515 (Aw).

((The resulting dry substance constituted the preferred embodiment of the present invention—a red grape dry composition)). The dry composition was sorted out manually to remove larger stems, and was, consequently, automatically ground into a consistent mass of pieces sized +/−⅛ inch. Grinding into a finer powder is also possible to meet specific objectives of the subject task.

The dry composition can be conveniently packed into a regular 3.20 g tea bag. Weight proportions of three components of the dry composition as allocated in the tea bag are shown in Table 1 below.

TABLE 1

| Component | Weight | % (in 3.20 g. bag) |
|---|---|---|
| 1. Berry stalks/stems | 0.20 g | 6.25 |
| 2. Skins | 1.00 g | 31.25 |
| 3. Seeds | 2.00 g | 62.50 |

Administration of Red Grape Dry Composition.

In one of the applications, the Red Grape Dry Composition may be used for human skin rejuvenation baths. Loose dry parcels, in the volume equal to approximately 1 cup, is placed into a muslin bag, or any bag made from porous cloth like cotton gauze or any other bag of loose weave fabric. The bag is either hung on the faucet with hot running water, or the herbs are simmered prior to arranging the bath in 4 cups of boiling water pouring the infusion into your water as/when ready. The color of the water becomes rosy. The duration of the bath should not exceed 15-20 minutes, with water temperature close or slightly higher that that of the human body. The cotton gauze bag can be used for skin scrubbing and massaging. Antibacterial rejuvenating properties of the red grapes affect the skin by anti-oxidizing skin cells, tightening and toning up the skin fabric.

(b) Embodiment: Red Grape Health Tea or Drink and the Method of its Preparation.

A total of 80 g of the dry composition was placed in 1 L of filtered hot water just before its boiling point. As the water reached the boiling point, the substance was stirred and kept simmering for 2 minutes. The contents were then steeped for 7-10 minutes, and, afterwards, filtrated into a clean stainless steel container to become the initial liquid base (hereinafter called "Round I Substance"—RI) for further processing. After boiling and filtration out of 1 L, 0.875 L remained. This RI constituted a base for consequential rounds of processing. Another portion of the dry composition of 80 g was placed in and mixed with RI (0.875 L). Then boiling, simmering activities as with RI was performed. The resulting liquid substance, Round II Substance (hereinafter referred as RII), was more concentrated in the volume of 0.698 L. Obviously, RII was heavier with a darker ruby color and a stronger lemon taste. This should indicate strong presence of Concord grape plant acids, mainly tartaric. The RII acidity was measured by Cornell Laboratory to be pH 3.79. Further, RII phenolic antioxidants were measured to show HPLC presence as follows: catechin 12 mg/L, tannin 264 mg/L, resveratrol (cis+trans) 0.8 mg/L, quercetin glycosides 23 mg/L, quercetin 4 mg/L, total antioxidants 11 mmol/L (ETS Laboratory Report #324068 of 01.18.2008). Additionally, RII content was analyzed in accordance with U.S. FDA food standard requirements. The results revealed low calories (10 per 240 g serving), and the presence of Vitamin C (10% DV) and Calcium (2% DV).

Further, Round III Substance (RIII) was prepared by placing 80 g of dry composition into RII 0.698 L, and by following the sequence of steps described for RI. At the end of the test, the liquid volume was 0.463 L. The resulting RIII HPLC properties were notably superior to those of RI and RII:

catechin 63 mg/L, tannin 454 mg/L, resveratrol (cis+trans) less than 1.0. mg/L, quercetin glycosides 20 mg/L, quercetin 4 mg/L, total antioxidants 20.6 mmol/L (ETS Laboratory Report #379509 of 02.03.2009). For the purpose of this embodiment, a limit of three rounds of processing was set. Interpretation of the RII and RIII data dynamics reveals a tendency towards greater catechin (+80%) and tannin (+41%) presence in RIII, while resveratrol, glycosides and quercetin remained almost unchanged. The HPLC dynamic in RII and RIII is demonstrated in Table 2.

TABLE 2

| HPLC Antioxidant | RII | RIII | % (change) |
| --- | --- | --- | --- |
| 1. Catechin | 12 mg/L | 63 mg/L | +80 |
| 2. Tannin | 264 mg/L | 454 mg/L | +/− |
| 3. Resveratrol (cis + trans) | 0.8 mg/L | 1.0 mg/L | +/− |
| 4. Quercetin glycosides | 23 mg/L | 20 mg/L | +/− |
| 5. Quercetin | 4 mg/L | 4 mg/L | 0 |
| Total | 11 mmol/L | 20.6 mmol/L | +46.6 |

Administration of Red Grape Health Drink/Tea.

The Red Grape Health drink (the term "tea or drink" coverers either of RI, RII or RIII) is to be taken as a food supplement, hot or cold, in the volume of 150-200 g, two-three times a day, between meals, at least 20 minutes prior to eating.

(a) RII was applied for treating common cold and proved to be effective. RII treatment was performed against severe Influenza on two volunteers: one a 56 year-old female, the other a 57 year-old male (inventor of the present invention). Both users did not receive flu shots at the beginning of the flu season, Fall of 2007. They were infected with a virus under different circumstances and at different times. The method of treating and the results were exactly the same and can be summarized in the following:

On the first day of feeling a cold a person was given 150 g of hot RII five times daily, between meals, at least 20 minutes prior to eating. This treatment method was administrated for a period of six days. Diet habits were modified, firstly, by increasing the intake of vegetables (especially onion and garlic), fresh fruits, buckwheat, oat and fish; secondly, by eliminating meats, fat, milk, cream, sugar, soft drinks, baked goods; and, thirdly, by reducing the overall daily caloric intake to 1500-1800 (as compared to US customary 2000-2500). No Aspirin or prescribed medications or antibiotics were taken during this period. Physical activities were reduced to the extent possible. The body was kept in a warm environment to allow it to rest and to ensure the temperature level needed for incoming antioxidants to work in synergy with the body's own immune system. No sick-days were taken from the work. Apparently, due to tartaric acid content in RII, the users felt a stronger appetite. Both RII users successfully recovered in six days time, with notable improvements in their health status having taken place after only the third day.

(b) RII was applied for treating high levels of cholesterol and blood glucose and proved to be effective. In this test, the inventor of the present invention (male, age 57, herein after referred to as volunteer) was taking RII with a goal to reduce blood cholesterol which had been in the range of 240-270 mg/dL over the period of the last ten years. The following technique was applied:

Before RII treatment commenced, the volunteer was on a normal diet. On the morning of Jan. 15, 2009, on an empty stomach, a blood test (before RII treatment commencement) was taken with the following results: glucose 84 mg/dL, cholesterol total 275 mg/dl, HDL 51 mg/dL, cholesterol/HDL ratio 5.4, LDL (calculated) 203 mg/dL, triglycerides 104 mg/dL. For the next 48 hours, the volunteer had followed strict "RII Diet" whereas no food was allowed, only hot RII in volumes of 200-400 grams, 4 times a day, (January 15, after blood test, 200 g; at lunch time, 400 g; at dinner time, 200 g; the same was repeated on January 16). A total of 1.6 L was taken. On the morning after the end of the treatment, January 17, a second blood test was taken on an empty stomach. Results showed a slight decrease in total cholesterol (from 275 to 271 mg/dl) with notable increase in "good cholesterol" HDL (from 51 to 59 mg/dL); cholesterol/HDL ratio also favorably changed from 5.4 to 4.6, thus moving into "normal health reference range."

Triglycerides results considerably improved, dropping from 104 to 29 mg/dL, showing a positive change of 72%.

Furthermore, RII demonstrated the ability to reduce[ing] blood glucose, [that] which dropped from 84 to 69 mg/dL, or approximately 18%. Other components of the metabolic panel have not shown any considerable changes.

Noted RII side effects were as follows: (i) during the 48 hour fasting period, the volunteer felt an increased appetite which could not be satisfied due to the test diet restriction; (ii) RII (RII and RIII) was noted to have a tightening affect on gastro-intestinal tract which can cause a longer food digesting periods.

(c) Another application of RII is that it is beneficial as a Facial Mask. Grape Facial Mask is made with a liquid composition: a clean white cloth is soaked in RII or RIII, then applied to the face for 10-15 minutes; the face is then wiped with a clean cloth, and moisturizing cream is applied to soften the skin. The treatment should be repeated twice a day, once in the morning, once at bedtime.

(d) RII or RIII liquid is used to prepare Grape Facial Spray (GFS). GFS is sprayed onto the face, in small portions, two-three times a day. Spray drops should be allowed to remain on the skin for a few seconds, then the face should be wiped up with a clean cloth, and then moisturizing cream should be applied to soften the skin. Concord grape antioxidants and vitamins defuse within skin fabric providing essential support to skin cells' healthy functioning.

Embodiments of the present invention including those related to human skin care are not limited by the preferred ones described above. Many more varieties and methods may exist in application of the disclosed dry and liquid compositions when mixed, combined, complemented, or subsequently used with other natural organic ingredients customary in the food and cosmetic industries. Those ingredients may include, but are not limited to: honey, dairy products, like butter milk, nut, olive, castor, other vegetable oils and others.

Thus, the scope of the embodiment should be determined by the appended claims and their legal equivalents, rather than examples given. The applicant expressly reserves the right to use all of or a portion of the content or claims as a base and/or additional description to broaden detailed support any of or all the claims or any element or component thereof. The applicant further reserves the right to move any portion of the incorporated content of such claim or any component thereof from the claim into the description or vice-versa as necessary to justify or present the subject matter as appropriately, or to obtain any benefit, or to comply with the patent law, rules and regulations of any country or treaty. All claims and content of the present application shall survive during the entire pendency of this application including any subsequent addition, continuation, detailing, division thereof or any reissue or extension thereon.

What is claimed:

1. A method for producing a nutraceutical drink for human consumption comprising the steps of:
   a) mixing the berries, stalks, skins and seeds of *Vitis labrusca* Concord grapes to form a composition, wherein the composition contains catechin, resveratrol, and quercetin;
   b) crushing said composition;
   c) subjecting the crushed composition to a first fermentation cycle for a suitable period of time to produce a first fermentation product consisting of a liquid and solids;
   d) separating the liquid from the first fermentation product, and subjecting the solids to a second fermentation cycle for a suitable period of time to produce a second fermentation product, wherein the first and second fermentation cycles are performed successively and without a chemical catalyst;
   e) drying the second fermentation product to produce a dried product, wherein said drying comprises sun drying and/or oven drying;
   f) grinding the dried product into a coarse or fine powder;
   g) steeping the powder in boiling water for a period of time to produce a nutraceutical drink having a content of catechin of about 63 mg/L and a content of resveratrol of about 1.0 mg/L therein.

2. The method for producing a nutraceutical drink for human consumption according to claim 1, wherein said dried product is sorted to remove the remaining stalks.

3. The method for producing a nutraceutical drink for human consumption according to claim 1, wherein said first fermentation cycle is carried out for a period of about eight days at about 72° F.

4. The method for producing a nutraceutical drink for human consumption according to claim 1, wherein only about 7-10% of said seeds are crushed before said first fermentation cycle.

5. The method for producing a nutraceutical drink for human consumption according to claim 1, wherein ambient yeast naturally present in said *Vitis labrusca* Concord grapes and stems catalyze said first and second fermentations and no acidity adjusting chemicals are employed during said method.

6. The method for producing a nutraceutical drink for human consumption according to claim 1, wherein said second fermentation cycle is about seven days at a temperature of about 60° F.

7. The method for producing a nutraceutical drink for human consumption according to claim 1, wherein said drying of the second fermentation product comprises exposing said second fermentation product to sun drying for a period of about 6 hours, followed by oven drying at about 180° F. for a period of about 10 hours.

8. The method for producing a nutraceutical drink for human consumption according to claim 7, wherein said oven drying is performed to attain a water activity of about 0.515 Aw.

9. The method for producing a nutraceutical drink for human consumption according to claim 1, wherein said dried product is manually sorted to remove stems and then ground to a product of particles with an average diameter of about 1/8 inch.

10. The method for producing a nutraceutical drink for human consumption according to claim 1, wherein said first and second fermentations cycles extend to no more than about a period of three weeks combined.

11. The method for producing a nutraceutical drink for human consumption according to claim 1, wherein the content of tannin of nutraceutical drink is about 454 mg/L.

* * * * *